(12) United States Patent
Khan et al.

(10) Patent No.: US 10,893,943 B2
(45) Date of Patent: Jan. 19, 2021

(54) METHOD AND APPARATUS FOR APPLYING A BONE ATTACHMENT COATING

(71) Applicant: Biomet Manufacturing, LLC, Warsaw, IN (US)

(72) Inventors: Mohammed Imran Khan, Berkshire (GB); Hannah Wilson, Avon (GB); Anthony Lane, Wiltshire (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/563,335

(22) PCT Filed: Apr. 11, 2016

(86) PCT No.: PCT/GB2016/051009
§ 371 (c)(1),
(2) Date: Sep. 29, 2017

(87) PCT Pub. No.: WO2016/162700
PCT Pub. Date: Oct. 13, 2016

(65) Prior Publication Data
US 2018/0064538 A1 Mar. 8, 2018

(30) Foreign Application Priority Data
Apr. 10, 2015 (GB) .................................. 1506122.9

(51) Int. Cl.
*A61F 2/30* (2006.01)
*A61F 2/34* (2006.01)
(Continued)

(52) U.S. Cl.
CPC ........ *A61F 2/30767* (2013.01); *A61F 2/3094* (2013.01); *A61F 2/34* (2013.01);
(Continued)

(58) Field of Classification Search
CPC .. C08K 3/34; C09D 5/00; B29B 15/10; A61F 2/30767
(Continued)

(56) References Cited

U.S. PATENT DOCUMENTS

| 6,139,913 A | 10/2000 | Van Steenkiste et al. |
| 6,261,402 B1 | 7/2001 | Watanabe et al. |

(Continued)

FOREIGN PATENT DOCUMENTS

| CN | 1688263 | 10/2005 |
| CN | 1781610 | 6/2006 |

(Continued)

OTHER PUBLICATIONS

"Chinese Application Serial No. 201680028395.3, Office Action dated Dec. 5, 2018", w English Translation, 13 pgs.
(Continued)

*Primary Examiner* — Dah-Wei D. Yuan
*Assistant Examiner* — Andrew J Bowman
(74) *Attorney, Agent, or Firm* — Schwegman Lundberg & Woessner, P.A.

(57) ABSTRACT

A method and apparatus for applying a bone attachment coating to a prosthetic component, the bone attachment coating being formed from a plurality of particles applied to a surface of the prosthetic component. The method comprising: locally exciting the particles so as to increase the kinetic and/or thermal energy of the particles; and applying pressure to the particles by virtue of a press arranged so as to press the particles against the surface of the prosthetic component at an interface between the press and the prosthetic component. The kinetic and/or thermal energy of the particles causes localised heating of the component such that the particles may be embedded into the surface of the prosthetic component.

20 Claims, 6 Drawing Sheets

(51) Int. Cl.
    *B05C 13/02*     (2006.01)
    *B29C 35/02*     (2006.01)
    *B29C 59/02*     (2006.01)
    *B05C 19/00*     (2006.01)
    *B05B 7/14*     (2006.01)
    *B05B 7/22*     (2006.01)
    *B05B 13/02*     (2006.01)
    *B05B 17/06*     (2006.01)
    *B05C 3/00*     (2006.01)
    *B05C 3/18*     (2006.01)
    *B05D 3/02*     (2006.01)
    *B05B 17/04*     (2006.01)
    *B05D 7/02*     (2006.01)

(52) U.S. Cl.
    CPC ............ *B05C 13/02* (2013.01); *B05C 19/004* (2013.01); *B29C 35/0261* (2013.01); *B29C 59/02* (2013.01); *A61F 2002/3093* (2013.01); *B05B 7/1486* (2013.01); *B05B 7/228* (2013.01); *B05B 13/0228* (2013.01); *B05B 17/04* (2013.01); *B05B 17/0623* (2013.01); *B05C 3/005* (2013.01); *B05C 3/18* (2013.01); *B05D 3/0254* (2013.01); *B05D 7/02* (2013.01); *B05D 2401/32* (2013.01); *B29C 2059/028* (2013.01)

(58) Field of Classification Search
    USPC ......................................................... 427/2.1
    See application file for complete search history.

(56) References Cited

U.S. PATENT DOCUMENTS

| | | | |
|---|---|---|---|
| 7,348,374 B2 * | 3/2008 | Martinazzo | C09D 5/033 427/522 |
| 2005/0197446 A1 * | 9/2005 | Loyen | B82Y 30/00 524/492 |
| 2005/0273176 A1 | 12/2005 | Ely et al. | |
| 2011/0311713 A1 | 12/2011 | O'neill et al. | |
| 2013/0018483 A1 * | 1/2013 | Li | B22F 3/105 623/23.55 |

FOREIGN PATENT DOCUMENTS

| | | | | |
|---|---|---|---|---|
| CN | 101405039 | | 4/2009 | |
| CN | 101730509 | | 6/2010 | |
| CN | 101883663 | | 11/2010 | |
| CN | 102333567 | | 1/2012 | |
| CN | 102458566 | | 5/2012 | |
| CN | 102490301 | | 6/2012 | |
| CN | 102500912 | | 6/2012 | |
| CN | 102500912 A | * | 6/2012 | ............ B23K 20/10 |
| CN | 103143804 | | 6/2013 | |
| CN | 103750924 | | 4/2014 | |
| CN | 103826680 | | 5/2014 | |
| CN | 107660141 | | 2/2018 | |
| EP | 2418169 A2 | | 2/2012 | |
| EP | 2614843 A2 | | 7/2013 | |
| FR | 2866578 | * | 8/2005 | ............ B29B 15/10 |
| FR | 2866578 A1 | | 8/2005 | |
| FR | 2975001 A1 | | 11/2012 | |
| FR | 3010931 A1 | | 3/2015 | |
| GB | 2537171 A | | 10/2016 | |
| JP | 09318801 A | | 12/1997 | |
| JP | H09318801 | | 12/1997 | |
| WO | WO-2009085618 A2 | | 7/2009 | |
| WO | 2015044605 | | 4/2015 | |
| WO | WO-2016162700 A1 | | 10/2016 | |

OTHER PUBLICATIONS

"International Application Serial No. PCT/GB2016/051009, International Search Report dated Jul. 11, 2016", 5 pgs.
"International Application Serial No. PCT/GB2016/051009, Written Opinion dated Jul. 11, 2016", 6 pgs.
"Chinese Application Serial No. 201680028395.3, Office Action dated Jul. 11, 2019", w English translation, 17 pgs.
"United Kingdom Application Serial No. 1506122.9, Office Action dated Apr. 14, 2015", 2 pgs.
"United Kingdom Application Serial No. 1506122.9, Search Report dated Sep. 16, 2015", 3 pgs.
"European Application Serial No. 16716663.6, Response filed Jun. 8, 2018 to Office Action dated Nov. 28, 2017", 17 pgs.
"International Application Serial No. PCT/GB2016/051009, International Preliminary Report on Patentability dated Oct. 19, 2017", 8 pgs.
"Chinese Application Serial No. 201680028395.3, Response Filed Mar. 19, 2019 to Office Action dated Dec. 5, 2018", (W/ English Claims), 14 pgs.
"Chinese Application Serial No. 201680028395.3, Response filed Sep. 26, 2019 to Office Action dated Jul. 11, 2019", (W/ English Claims), 14 pgs.
"United Kingdom Application No. 1506122.9, Office Action dated Mar. 16, 2020", 4 pgs.
"United Kingdom Application No. 1506122.9, Response filed May 18, 2020 to Office Action dated Mar. 16, 2020", 11 pgs.
"United Kingdom Application Serial No. 1506122.9, Intent to Grant Under Section 18(4) dated Jul. 8, 2020", 2 pages.

* cited by examiner

METHOD AND APPARATUS FOR APPLYING A BONE ATTACHMENT COATING

This application is a U.S. National Stage Application under 35 U.S.C. 371 from International Application Serial No. PCT/GB2016/051009, filed on Apr. 11, 2016, and published as WO 2016/162700 A1 on Oct. 13, 2016, which claims priority to United Kingdom Application No. 1506122.9, filed on Apr. 10, 2015, the benefit of priority of each of which is claimed hereby, and each of which are incorporated by reference herein in its entirety.

The present disclosure relates to a method and apparatus for applying a bone attachment coating, in particular to a prosthetic component.

BACKGROUND

Traditional prosthetic acetabular cups comprise an outer metallic cup and an inner liner typically made from a polymer material. Coatings may be added to the metallic up to enhance bone fixation. Modular systems comprising a metal cup and plastic liner are however expensive and there is a need for a lower cost acetabular cup that is capable of high volume manufacture, A previously-proposed solution to this problem has been to manufacture the outer cup and inner liner as one component. This is known as a monoblock. It is desirable that the material selected for the monoblock closely approximates the stiffness, e.g. elastic modulus, of the bone into which the orthopaedic component is implanted to improve stress transfer and fixation and reduce stress shielding. In this regard, ceramic monoblock cups have been tried (see for example US20050273176A1), but these lacked a similar elastic modulus to bone and therefore were generally found unsuitable.

By contrast, the use of biocompatible polymer, such as polyethylene, e.g. Ultra-High-Molecular-Weight Polyethylene (UHMWPE), polyurethanes or other polymer-based materials, such as Carbon Fibre Reinforced PolyEther-Ether-Ketone (CFR-PEEK), have been favoured as they have a stiffness close to that of bone. Furthermore, such polymers have good load distribution, can adapt to deformations of the pelvis, prevent stress shielding and have a lower material cost compared to ceramic. An example of a polyethylene monoblock cup is disclosed in FR2975001. This document describes a cup made of plastic with substantially the entire outer surface of the cup being coated with an osteo-conductive metal for contacting the acetabulum.

Coatings are generally applied to a prosthetic component as a spray. For example, particles or powder of the material to be sprayed may be injected into a gas (such as helium, argon, nitrogen or hydrogen) and the gas and material may be projected from a spray nozzle at a relatively high velocity. Further, in thermal type spray methods, a high temperature plasma or gas flame may be utilized. Such flame temperature may be over 2000° C.

However, semi-crystalline polymeric materials, such as UHMWPE, have a relatively low melting point (typically 130° C.). Once heated above the materials melting point, the physical structure, mechanical and chemical (oxidative) properties may be changed. This change can adversely affect the strength and wear properties and durability as an orthopaedic bearing surface.

Accordingly, it is desirable to be able to apply a material that encourages bone attachment) onto a polymer surface of an orthopaedic implant (e,g. UHMWPE) in a mass-production process without causing permanent physical or chemical changes to the properties of the polymer,

STATEMENTS OF INVENTION

According to a first aspect of the present disclosure there is provided a method of applying a bone attachment coating to a prosthetic component, the bone attachment coating being formed from a plurality of particles applied to a surface of the prosthetic component, the method comprising:
exciting the particles so as to increase the energy, e.g. kinetic, vibrational and/or thermal energy, of the particles;
wherein the energy of the particles causes localised heating of the prosthetic component such that the particles may be embedded into a bone facing region, e.g. the surface, of the prosthetic component.

The particles may be excited with energy in a form (e.g. type of energy, frequency, intensity, direction) that is preferentially absorbed by the particles and without substantially heating the prosthetic component.

The method may comprise using ultrasound to excite the particles, e.g. to increase the vibrational energy of the particles. The particles may be excited by an ultrasonic exciter or emitter. The ultrasonic emitter may provide a surface at the interface with the prosthetic component. Additionally or alternatively, the method may comprise using electro-magnetic energy to excite, e.g. thermally excite, the particles. Advantageously, such processes are fast, easily automated and have low thermal impact on the materials involved.

The method may comprise heating the particles. For example, the particles may be heated by virtue of radiation, e.g. microwaves, or conduction from a surrounding medium, such as a fluid, e.g. supercritical $CO_2$ forming a fluidised bed. In another example, the method may comprise using a magnetic field to induce electric currents within the particles, thereby heating the particles. The particles may be pre-heated prior to being energised by any of the above-described methods.

The exciter, e.g. ultrasonic exciter, may apply a pressure to the particles to force them into the prosthetic component, e.g. at an interface between the exciter and the prosthetic component. The method may additionally comprise applying pressure to the particles by virtue of a press arranged so as to force, e.g. press, the particles against the surface, e.g. into the bone facing region, of the prosthetic component. The ultrasonic emitter may be provided between the press and the prosthetic component, e.g. such that the ultrasonic emitter provides a pressing surface. The press may apply a pressure to the prosthetic component and force the prosthetic component towards the ultrasonic exciter and the particles.

The method may comprise providing the particles at an interface between the energy exciter or press and the prosthetic component. For example, the method may comprise dispensing the particles from a dispenser. The particles may flow from the dispenser to the interface by virtue of gravity and/or under pressure. The dispenser and/or particles may be agitated so as to encourage the flow of the particles from the dispenser. Additionally or alternatively, the method may comprise providing the particles at the interface between the energy exciter or press and the prosthetic component by virtue of carrying the particles in a flow of a fluid.

The method may comprise moving the prosthetic component, energy exciter and/or press so that the particles may be applied over the surface of the prosthetic component. For example, the method may comprise rotating the prosthetic component and the energy exciter relative to one another, e.g. about a first axis of the prosthetic component. The prosthetic component and the energy exciter may be rotatable relative to one another about a second axis of the prosthetic component. A rotational rate about the first or second axis may be adjusted, e.g. according to a position of the prosthetic component about the second or first axis respectively.

The method may comprise monitoring the density of the particle distribution on the surface of the prosthetic component. A velocity at which the prosthetic component and press may be moved relative to one another may be varied to account for any variation in the particle density, e.g. if the density is too low the velocity may be reduced or vice versa.

According to a second aspect of the present disclosure there is provided an apparatus for applying a bone attachment coating to a prosthetic component, the bone attachment coating being formed from a plurality of particles applied to a surface of the prosthetic component, the apparatus comprising:

an exciter configured to excite, e.g. locally, the particles so as to increase the energy, e.g. kinetic, vibrational and/or thermal energy, of the particles:

wherein the energy of the particles causes localised heating of the prosthetic component such that the particles may be embedded into a bone facing region, e.g. the surface, of the prosthetic component.

The particles may be excited with energy in a form that is preferentially absorbed by the particles and without substantially heating the prosthetic component.

The exciter may comprise an ultrasonic exciter or emitter, e.g. to increase the vibrational energy of the particles. The ultrasonic emitter may provide a surface at the interface with the prosthetic component. Additionally or alternatively, the exciter may comprise an electro-magnetic energy emitter.

The exciter may comprise a heater configured to heat the particles. For example, the heater may heat the particles by virtue of radiation, e.g. microwaves, or conduction from a surrounding medium, such as a fluid, e.g. supercritical $CO_2$ forming a fluidised bed. In another example, the heater may be configured to induce electric currents within the particles by virtue of a magnetic field. Additionally or alternatively, a pre-heater may be provided to pre-heat the particles prior to being energised by any of the above-described methods.

The apparatus may further comprise a press arranged so as to force, e.g. press, the particles against the surface, e.g. into the bone facing region, of the prosthetic component. The exciter, e.g. ultrasound exciter, may be provided between the press and the prosthetic component or the prosthetic component may be provided between the press and the exciter.

The apparatus may be configured to provide the particles at an interface between the energy exciter or press and the prosthetic component. For example, the apparatus may comprise a dispenser configured to dispense the particles. The dispenser may be arranged such that the particles may flow from the dispenser to the interface by virtue of gravity and/or by virtue of an applied pressure. The apparatus may comprise an agitator configured to agitate the dispenser and/or particles so as to encourage the flow of the particles from the dispenser. Additionally or alternatively, the apparatus may be configured to provide the particles at the interface between the energy exciter or press and the prosthetic component by virtue of carrying the particles in a flow of a fluid.

The prosthetic component, exciter and/or press may be movable so that the particles may be applied over the surface of the prosthetic component. For example, the prosthetic component and the energy exciter or may be rotatable relative to one another, e.g. about a first axis of the prosthetic component. The prosthetic component and the energy exciter or may be rotatable relative to one another about a second axis of the prosthetic component. The apparatus may comprise a controller configured to adjust a rotational rate about the first or second axis, e.g. according to a position of the prosthetic component about the second or first axis respectively.

The dispenser may also move relative to the prosthetic component, e.g. the dispenser may be coupled to the energy exciter and/or press and the dispenser and energy exciter and/or press may thus move together relative to the component.

The dispenser may comprise an outlet through which the particles may be dispensed. The rate at which the particles leave the outlet may vary across the outlet. Such a variation may account for the rate at which the outlet passes over the prosthetic component surface varying across the outlet, e.g. due to the geometry of the prosthetic component and/or the relative rotation between the components. For example, a width of the dispenser outlet may vary along a length of the dispenser outlet. In another example the outlet may be formed by a number of openings and the density or size of such openings may vary across the outlet. Such variations may ensure an even density distribution of the particles over the surface of the prosthetic component.

The apparatus may comprise a sensor configured to monitor the density of the particle distribution on the surface of the prosthetic component. A controller may vary the velocity at which the prosthetic component and press may be moved relative to one another to account for any variation in the particle density, e.g. if the sensed particle density is too low the velocity may be reduced or vice versa.

The apparatus, e.g. press or exciter, may comprise a pressing surface configured to press the particles against the prosthetic component surface. The pressing surface may be textured, e.g. comprising peaks and troughs. Additionally or alternatively, the prosthetic component surface may be textured, e.g. comprising peaks and troughs.

The particles may comprise titanium, titanium alloy, tantalum, niobium, other refractory metals or alloys thereof, cobalt-chromium alloy, stainless steel, bio-ceramics, Bioglass® or any other osteoconductive or osteoinductive material (such as Hydroxyapatite). The prosthetic component may be made from a polymer, such as Polyethylene, Ultra-High-Molecular-Weight Polyethylene (UHMWPE), Polyurethanes, Polyetheretherketone (PEEK), Polyaryletherketone (PAEK), Polyetherketoneketone (PEKK), Carbon-fibre-reinforced Polyetheretherketone (CFR-PEEK) or any other polymer-based material.

BRIEF DESCRIPTION OF THE DRAWINGS

For a better understanding of the present disclosure, and to show more clearly how it may be carried into effect, reference will now be made, by way of example, to the accompanying drawings, in which.

DETAILED DESCRIPTION

Figure 1:
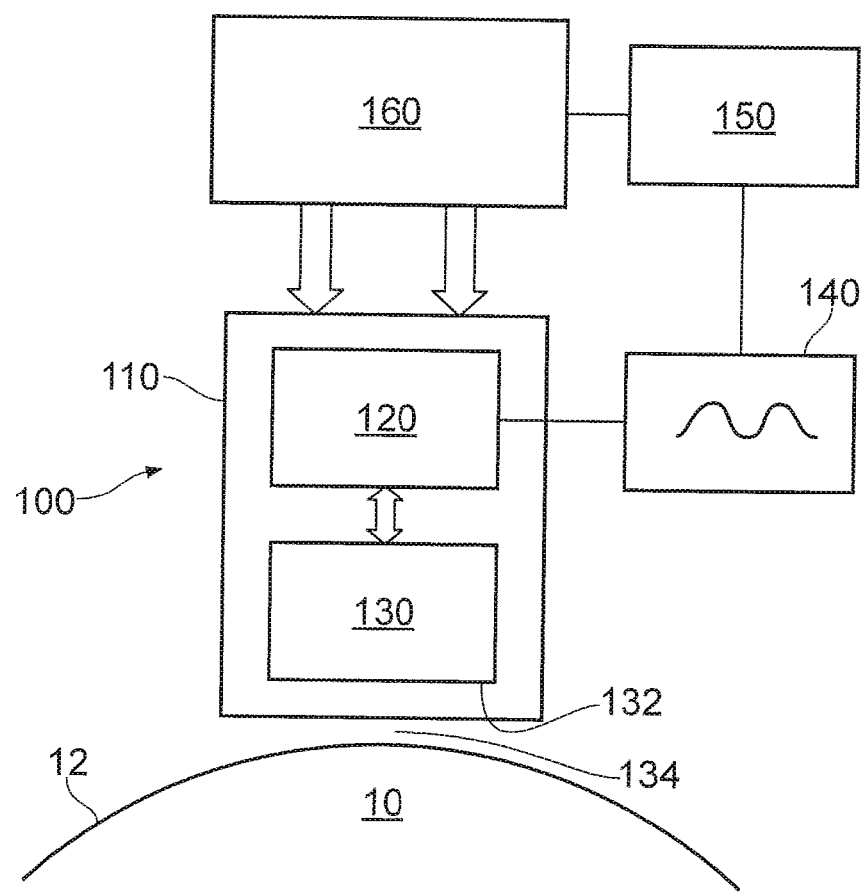
FIG. 1 shows a schematic view of an apparatus for applying a bone attachment coating to a prosthetic component.
Figure 2A:
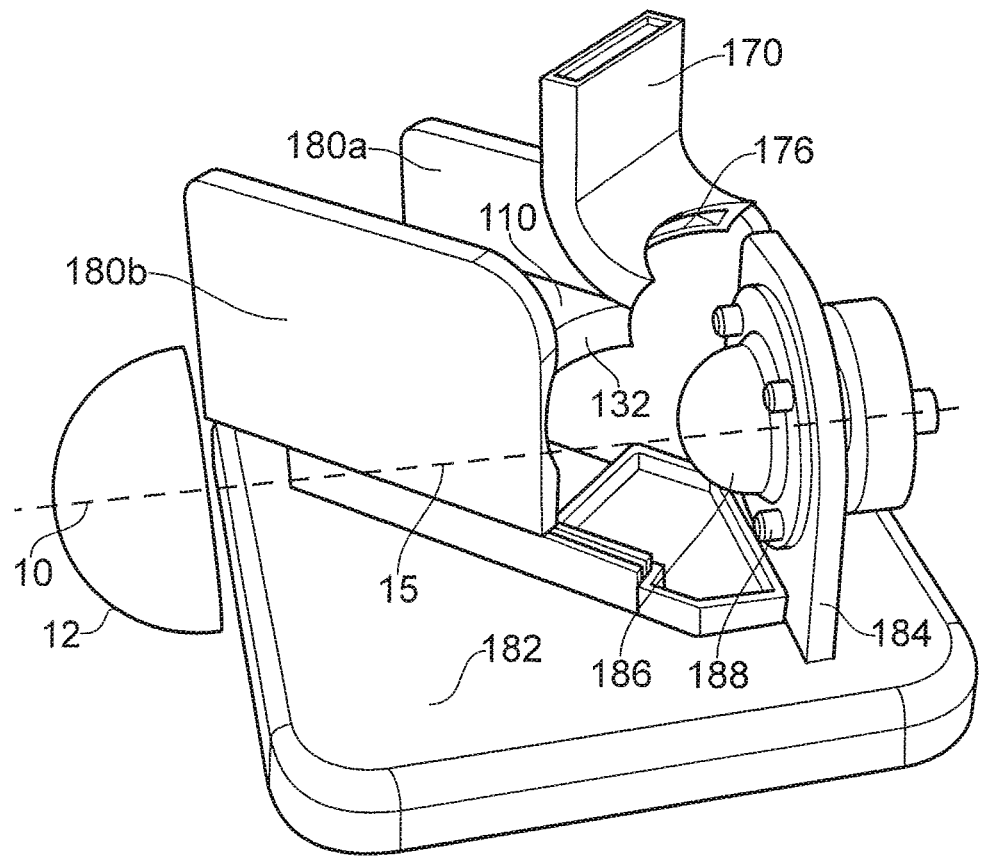
FIGS. 2(a) and 2(b) show exploded views of an apparatus for applying a bone attachment coating to a prosthetic component.
Figure 2B:
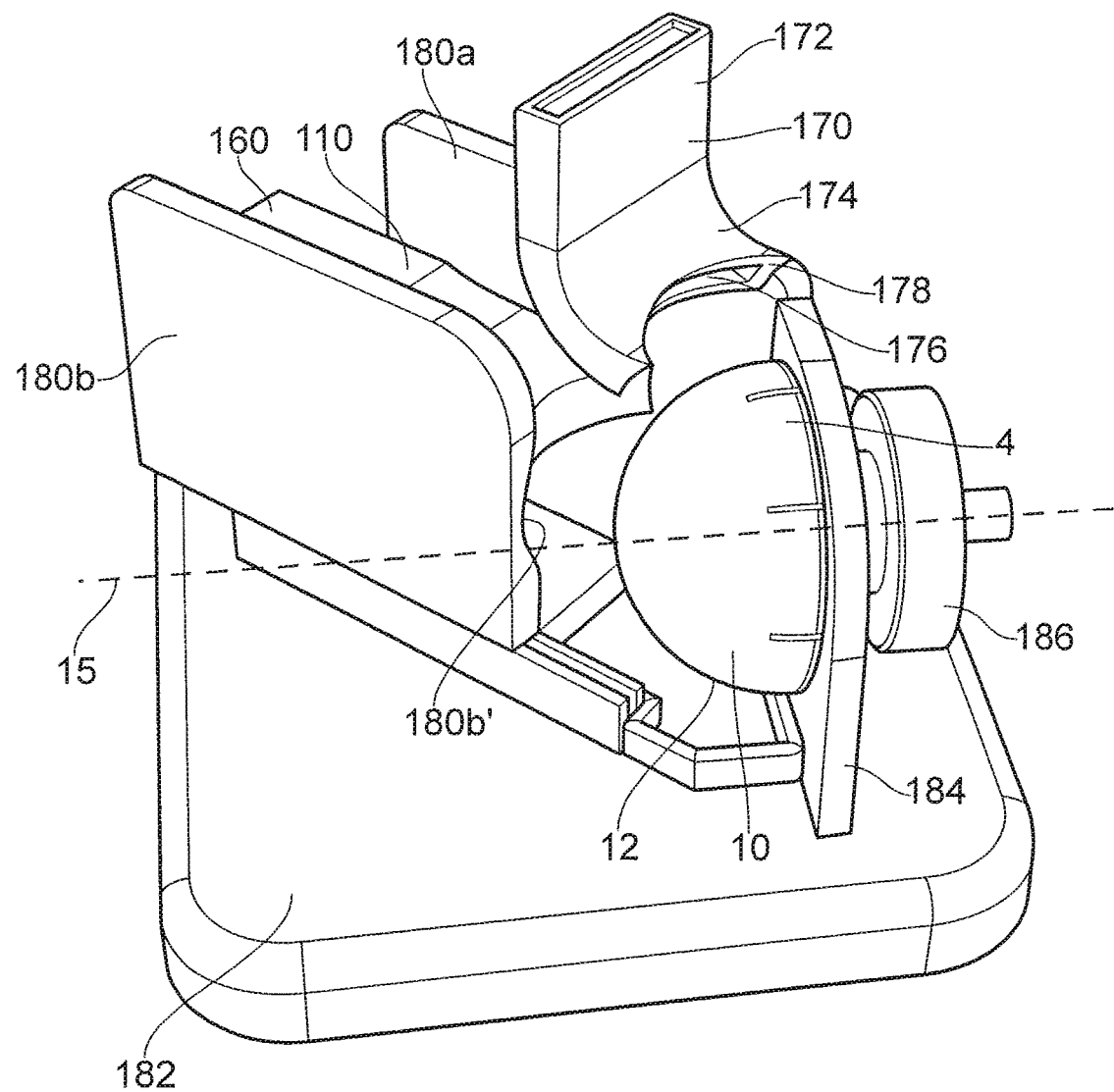

With reference to FIGS. 1, 2(a) and 2(b), the present disclosure relates to an apparatus 100 for applying a bone attachment coating to a prosthetic component 10. The bone attachment coating is formed from a plurality of discrete particles and the particles are applied to a bone facing surface 12 of the prosthetic component 10. The particles may be made from a material that encourages bone growth and/or attachment, for example metals (such as titanium, titanium alloy, tantalum, niobium, other refractory metals, cobalt-chromium alloy, stainless steel or alloys thereof), ceramics (such as bio-ceramics or Bioglass®) or any other osteoconductive or osteoinductive material (such as Hydroxyapatite). The particles may initially be in a powder form. The prosthetic component may be made from a polymer, such as Polyethylene, Ultra-High-Molecular-Weight Polyethylene (UHMWPE), Polyurethanes, Polyetheretherketone (PEEK), Polyaryletherketone (PAEK), Polyetherketoneketone (PEKK), Carbon-fibre-reinforced Polyetheretherketone (CFR-PEEK) or any other polymer based material.

The apparatus 100 comprises an exciter configured to excite the particles so as to increase their kinetic and/or thermal energy. The exciter may be configured to locally excite the particles, e.g. in the immediate vicinity of the exciter, without directly exciting the prosthetic component surface 12. The exciter may excite the plurality of particles at the same time. The exciter may excite the particles by directing energy at the particles which is preferentially absorbed by the particles and not the prosthetic component. In other words, the exciter may comprise an energy source which emits energy in a form that is absorbed by, e.g. resonates, the particles, but not the prosthetic component surface in a significant way. Accordingly, the prosthetic component surface 12 may substantially only be heated by virtue of the energy of the particles. As a result, the energy imparted to the prosthetic component surface 12 and the resulting effect on the material properties may be minimised.

In the particular example shown, the exciter may comprise an ultrasonic exciter 110 configured to increase the vibrational energy of the particles. The ultrasonic exciter may comprise a transducer 120 to convert an electrical signal into a mechanical vibration. The transducer 120 may comprise one or more piezoelectric elements. The ultrasonic exciter 110 may further comprise a sonotrode or horn 130 to apply the mechanical vibration to the coating particles. The sonotrode 130 may be made from a metal, such as titanium, aluminium, steel; a polymer; or any other suitable material.

The transducer 120 and sonotrode 130 may be operatively connected so that the sonotrode is vibrated by the transducer. Both the transducer 120 and sonotrode 130 may be tuned to resonate at the same ultrasonic frequency, for example at a frequency between 5 kHz and 60 kHz.

The apparatus 100 may further comprise an electronic ultrasonic generator 140, which is configured to deliver an AC signal with a frequency substantially matching the resonant frequency of the ultrasonic exciter. A controller 150 may be operatively coupled to the ultrasonic generator. The controller 150 may control the delivery of the ultrasonic energy.

The apparatus 100 further comprises a press 160 arranged so as to apply a pressure to the particles and press the particles against the surface of the prosthetic component. Although not depicted, it will be appreciated that the press 160 may apply pressure by virtue of an actuator, such as a hydraulic, pneumatic, electro-mechanical or any other type of actuator. At least a portion of the press, e.g. part of the actuator, may be unitary with the exciter.

The above-mentioned controller 150 or a separate controller may be operatively coupled to the press 160. The controller may control the force applied by the press, e.g. by the actuator.

In the particular example shown, the press 160 is configured to move the ultrasonic exciter 110 towards the prosthetic component. The press may be coupled to any point on the ultrasonic exciter, e.g. at an end of the exciter as shown. However, in an alternative arrangement, the press may be coupled to a point on the sonotrode that is a vibrational node at the resonant frequency. In a further alternative arrangement, the press may move the prosthetic component 10 towards the exciter and a portion of the exciter may be held in place by a rigid structure. The press may apply a force such that the exciter and prosthetic component are compressed together. (The exciter may then provide an additional compressive force.) However, the press may simply bring the exciter and prosthetic component towards each other and a compressive force may be provided by the exciter.

The sonotrode 130 comprises an interface surface 132 that forms an interface 134 with the prosthetic component surface 12. The particles may be provided between the sonotrode interface surface 132 and the prosthetic component surface 12. The interface surface 132 may press the particles against the prosthetic component surface by virtue of the pressure applied by the press and the vibrational forces applied by the exciter.

Figure 3A:
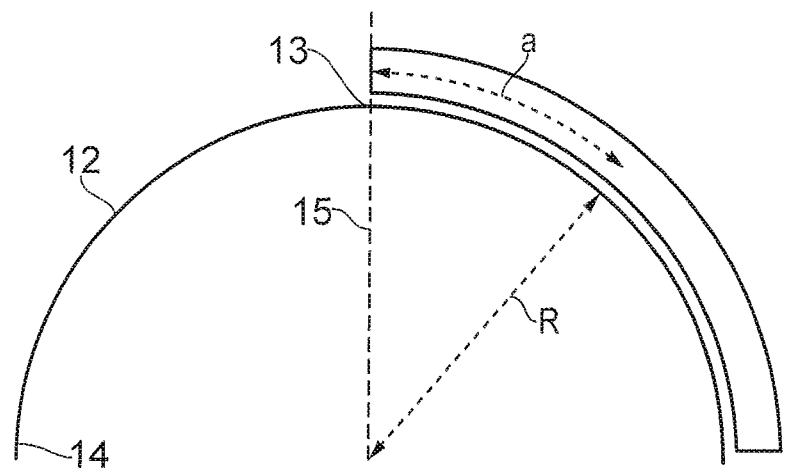
FIGS. 3(a) and 3(b) show schematic side sectional and end on views respectively of the dispenser outlet.
Figure 3B:
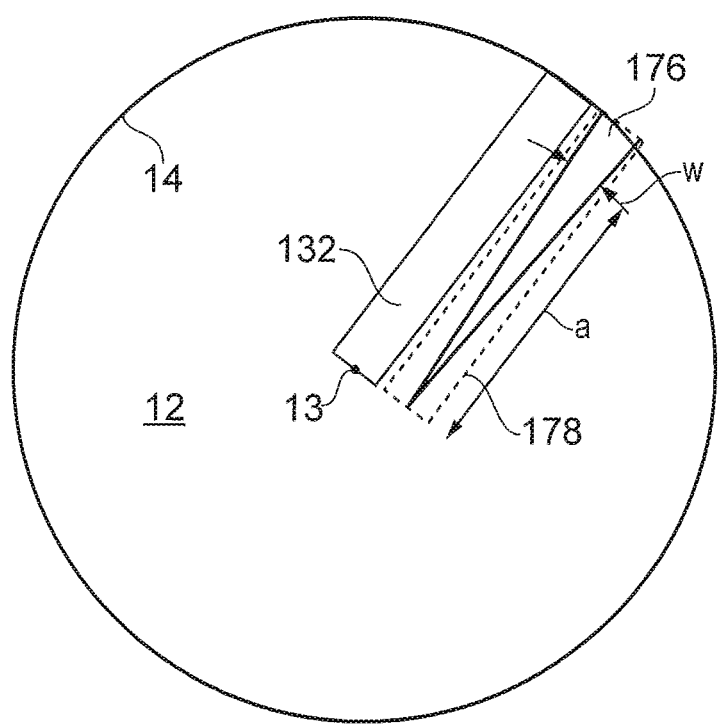

The sonotrode 130 may extend over a portion of the prosthetic component surface 12 and the sonotrode interface surface 132 may be shaped to correspond to the shape of the prosthetic component surface 12. For example, the sonotrode interface surface 132 may define an arc corresponding to a contour of the prosthetic component surface 12. In the particular example shown, the prosthetic component 10 may be substantially hemispherical, e.g. in the case of the prosthetic component being an acetabular cup, and the sonotrode interface surface 132 may define a circular arc. As depicted in FIG. 3, the sonotrode interface surface 132 may extend from a rim 14 of the prosthetic component to a pole or midpoint 13 on the component surface 12. Accordingly, in the case of the prosthetic component being hemispherical, the sonotrode interface surface 132 may define a circular arc subtended by 90°.

With reference to FIGS. 2(a) and 2(b), the apparatus 100 may be configured to provide the particles at the interface between the sonotrode 130 and the prosthetic component 10. For example, the apparatus may comprise a dispenser 170 configured to feed the particles onto the interface 134. The dispenser 170 may comprise a store section 172, which may store the plurality of discrete particles, which may be in powder form, prior to being applied to the prosthetic component surface 12. The dispenser may comprise a feed section 174 with an outlet 176 through which the particles may be dispensed. The particles may pass from the store section 172 to the feed section 174 and then out of the outlet 176. The store section 172 may be placed above the feed section to aid transfer of the particles from the store section 172 to the feed section 174.

The dispenser 170 may be arranged such that the particles may flow from the dispenser to the sonotrode interface 134 by virtue of gravity. For example, the dispenser outlet 176 may be arranged above the sonotrode interface such that the particles dispensed from the dispenser outlet 176 fall into the interface where they are excited and embedded into the prosthetic component. Additionally or alternatively, the particles may be placed under pressure to encourage them to flow out of the outlet 176.

Further still, the apparatus 100 may comprise an agitator configured to agitate the dispenser and/or particles so as to encourage the flow of the particles from the dispenser. Such agitation may be provided by coupling the dispenser 170 to the sonotrode 130. However, it is also envisaged that the dispenser 170 and sonotrode 130 may be separate components.

In a further alternative arrangement (not shown), the apparatus may be configured to provide the particles at the interface between the press and the prosthetic component by virtue of carrying the particles in a flow of a fluid, such as air, argon, nitrogen or any other fluid.

The outlet 176 may be provided on an end face 178 of the dispenser 170. The outlet 176 and end face 178 may extend over a portion of the prosthetic component surface 12. Accordingly, the end face 178 (and outlet) may be shaped to correspond to the shape of the prosthetic component surface 12. For example, the outlet 176 may define an arc corresponding to a contour of the prosthetic component surface 12. In particular, the prosthetic component 10 may be substantially hemispherical, e.g. in the case of the prosthetic component being an acetabular cup, and the outlet may define a circular arc. As depicted, the outlet 176 may extend from the rim 14 of the prosthetic component to the midpoint 13 on the component surface 12. Accordingly, in the case of the prosthetic component being hemispherical, the outlet may define a circular arc subtended by 90°.

The apparatus 100 may further comprise a pair of side walls 180a, 180b, which may extend from a base 182. The side walls 180a, 180b may be provided either side of the press 160, exciter 110 and dispenser 170. The side walls 180a, 180b may support the press 160, exciter 110 and/or dispenser 170. The exciter 110 may be slidably disposed between the side walls 180a, 180b. The press 160 may be coupled to the side walls 180 and/or base 182 so that the press can move the exciter towards the prosthetic component.

Edges of the side walls 180 may be provided either side of the sonotrode interface 134 and may provide a barrier to the particles to help retain the particles at the interface. Accordingly, one of the side walls 180a may be provided at a first end of the interface 132, e.g. adjacent to the rim 14 of the prosthetic component. The other of the side walls 180b may be provided at a second end of the interface 132, e.g. adjacent to the midpoint 13 on the component surface 12. The edge of side wall 180b may be shaped to receive the prosthetic component. In the case of the prosthetic component being substantially hemispherical, the side wall 180b may have curved cut-out 180b' corresponding to the curvature of the prosthetic component.

One or both of the side walls 180a, 180b may be movable, e.g. slidable, relative to the base 182. In particular, moving the side wall 180b, and thus the exciter 110, away from the prosthetic component 10 may facilitate removal and attachment of the prosthetic component.

The side walls 180 may be angled, e.g. oblique, with respect to an axis 15 of the prosthetic component 10. The axis 15 may pass through the midpoint 13 on the surface 12 and the prosthetic component may be axially symmetric about the axis 15. It will be appreciated that the press 160, exciter 110 and/or dispenser 170 provided between the side walls may also be angled with respect to the axis 15 of the prosthetic component 10. In the particular example shown, the side walls 180, press 160, exciter 110 and/or dispenser 170 are angled at 45 to the axis 15.

The prosthetic component 10 may be rotated relative to the exciter 110 and the prosthetic component 15 may be rotated about axis 15 of the prosthetic component. In this way the sonotrode interface surface 132 may pass over substantially all of the prosthetic component surface 12 as the prosthetic component 12 rotates.

The rotation of the prosthetic component about the axis 15 may be in a direction that encourages the particles from the dispenser outlet 176 to the sonotrode interface 134, e.g. in a downwards direction at the outlet 176.

The apparatus 100 may further comprise a support member 184 for supporting the prosthetic component 10. As depicted, the support member 184 may be in the form of a wall extending from the base 182. A rotatable member 186 may be supported by the support member 184. The rotatable member 186 may receive the prosthetic component 10 and may hold the prosthetic component by virtue of one or more features 188 so that the prosthetic component 10 rotates with the rotatable member 186. The features 188 may engage corresponding features provided on the prosthetic component or the features may frictionally engage a surface of the prosthetic component. FIGS. 2(a) and 2(b) show the apparatus before and after attachment of the prosthetic component to the rotatable member 186 respectively.

The rotatable member 186 may be attached to a drive unit, such as a motor. Controller 150 or a separate controller may control rotation of the drive unit. The controller may adjust a rotational rate of the prosthetic component 10 about the axis 15.

To ensure an even coverage of the particles on the surface 12 of the component, the outlet 176 may be configured to vary the rate at which the particles leave the outlet depending on where the particles leave the outlet. Such a variation may account for the fact that the rate at which the outlet 176 passes over the surface 12 varies across the outlet, e.g. due to the geometry of the prosthetic component and/or the relative rotation between the components. For example, with reference to FIGS. 3(a) and 3(b), the width, w, of the outlet 176 may vary with the arcuate distance, a, from the midpoint 13 on the prosthetic component surface 12, thereby allowing the flow rate of particles out of the outlet to change along the outlet. In particular, in the case of the prosthetic component being at least partially hemispherical, the width, w, may vary in proportion to the sine of a ratio of the distance, a, to the outer radius, R, of the prosthetic component, i.e. according to the following relationship:

$$w \propto \sin\left(\frac{a}{R}\right).$$

In another example the outlet 176 may be formed by a plurality of openings and the density or size of such openings may vary across the outlet according to a relationship similar to that described above. Such variations may ensure an even density distribution of the particles over the prosthetic component surface 12. In a further example, the sonotrode surface 132 may have a width that is governed by the above-described relationship.

Furthermore, the apparatus may comprise a sensor (not shown) configured to monitor the density of the particle distribution on the surface. The sensor may use a non-destructive imaging technique, e,g, by virtue of a Charge-Coupled Device (CCD) detector, thermography, electrical current or any other means. The monitoring of the density may occur after the particles have been applied to the surface or during application. In the latter case, the controller may vary the velocity at which the prosthetic component is moved relative to the sonotrode 130 to account for any variation in the particle density, e.g. if the sensed particle density is too low the velocity may be reduced or vice versa.

In an alternative arrangement (not depicted), the prosthetic component 10 may be rotated about a further axis of the prosthetic component. For example, the further axis may be perpendicular to the axis 15 and in the case of the prosthetic component being hemispherical may pass through the rim 14 of the prosthetic component. Such additional rotation may be useful if the outlet 176 and sonotrode interface 134 do not extend all the way from the rim 14 to the midpoint 13 on the component surface 12, e.g. the arc of the outlet 176 and sonotrode interface 134 is subtended by an angle less than 90°. Rotation about the further axis may allow the outlet 176 and sonotrode interface 134 to pass over the region from the rim 14 to the midpoint 13. In such an alternative arrangement, the controller may adjust a relative rotational rate about the axis 15 depending on the position of the prosthetic component about the further axis to ensure an even coating of particles. For example, the prosthetic component may be rotated more slowly about the axis 15 when the sonotrode is closer to the rim.

Alternatively, the controller may adjust a relative rotational rate about the further axis depending on the position of the prosthetic component about the axis 15 to ensure an even coating of particles. For example, the prosthetic component may be rotated more slowly about the further axis when the sonotrode is closer to the rim.

In a further alternative arrangement (not depicted), the exciter, press and/or dispenser may be movable relative to the prosthetic component, e.g. rotatable about the axis 15 and/or the further axis, so that the particles may be applied over the surface of the prosthetic component. For example, the prosthetic component may rotate about axis 15 and the exciter press and/or dispenser may rotate about the further axis or vice versa.

Although not depicted, the apparatus 100 may be provided in a sealable chamber. To reduce degradation of polymer-based material during operation of the apparatus, the sealed chamber may be under a vacuum or may be filled with an inert gas, such as nitrogen or a noble gas, e.g. argon.

Figure 4A:
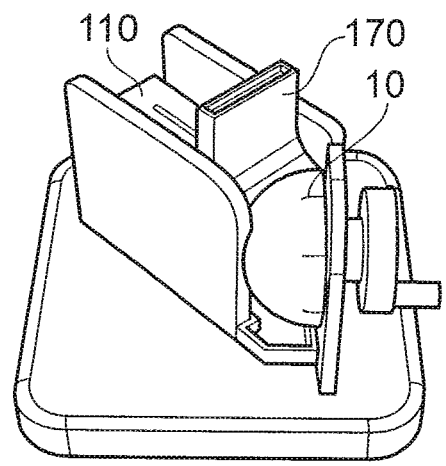
FIGS. 4(a), 4(b) and 4(c) depict steps in a method of applying a bone attachment coating to a prosthetic component.
Figure 4B:
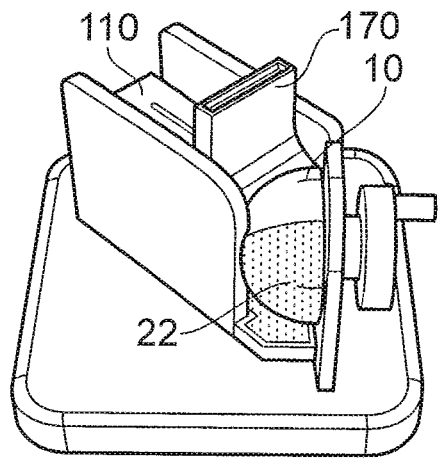
Figure 4C:
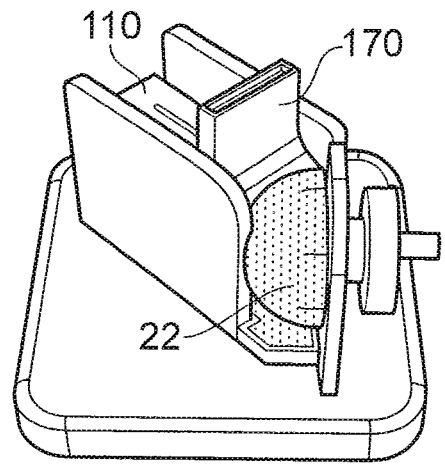
Figure 5A:
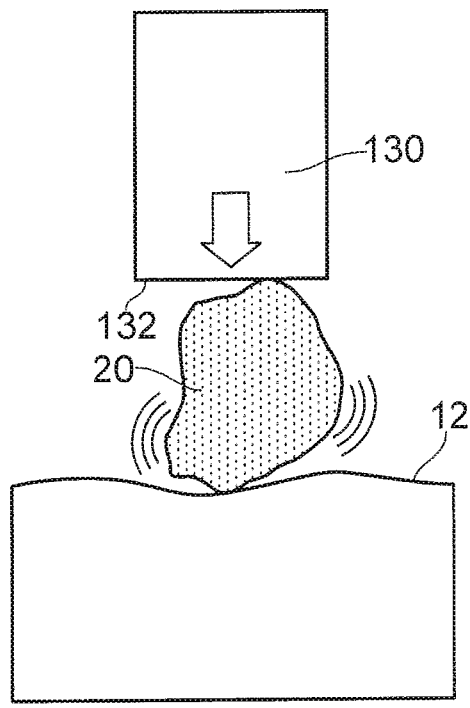
FIGS. 5(a) and 5(b) show a side view of the particles before and after embedding in the surface of the prosthetic component.
Figure 5B:
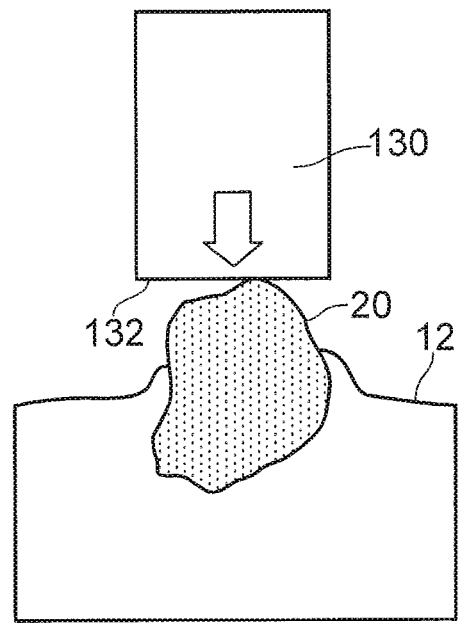

With reference to FIGS. 4(*a*)-(*c*) and 5(*a*)-(*b*), operation of the apparatus 100 for applying a bone attachment coating to the prosthetic component will now be explained. FIGS. 4(*a*)-(*c*) show the progression of the bone attachment coating being applied to the prosthetic component surface. FIGS. 5(*a*)-(*b*) show a sample particle before and after the particle is embedded into the prosthetic component respectively.

Prior to the application of the particles to the prosthetic component 10, the surface 12 of the prosthetic component may be pre-treated, e.g. with solvent or adhesive, to improve adhesion and to facilitate retention of the particles at the surface. The particles may also be pre-heated before being provided in the dispenser or excited by the exciter. For example, the dispenser may comprise a heater for pre-heating the particles.

The prosthetic component 10 may be attached to the rotatable member 186 and the side wall 180*b*, exciter 110 and dispenser 170 may be brought into close proximity with the prosthetic component 10. With the dispenser 170 loaded with particles, the exciter 110 may then be activated. The prosthetic component 10 may be rotated to pass the exciter 110 over the surface 12 of the prosthetic component 10.

Ultrasonic vibration from the transducer 120 is introduced through the sonotrode 130 into the particles 20 held at the interface 134. The vibrational energy is selected to cause localised heating and subsequent melting of the surface 12 of the prosthetic component 10 through friction of the particle movement at the interface 134. The vibrational energy is selected to be lower than the energy required to melt the particles 20. Embedding of the bone attachment particles 20 occurs within the surface of the polymer part as a result of the softening of the polymeric surface under the localised heating, high-pressure impaction and local motion of the bone attachment particles.

Fixation of the particles occurs after subsequent cooling and hardening of the polymeric material resulting in a surface coating 22 of bone attachment material.

Figure 6:
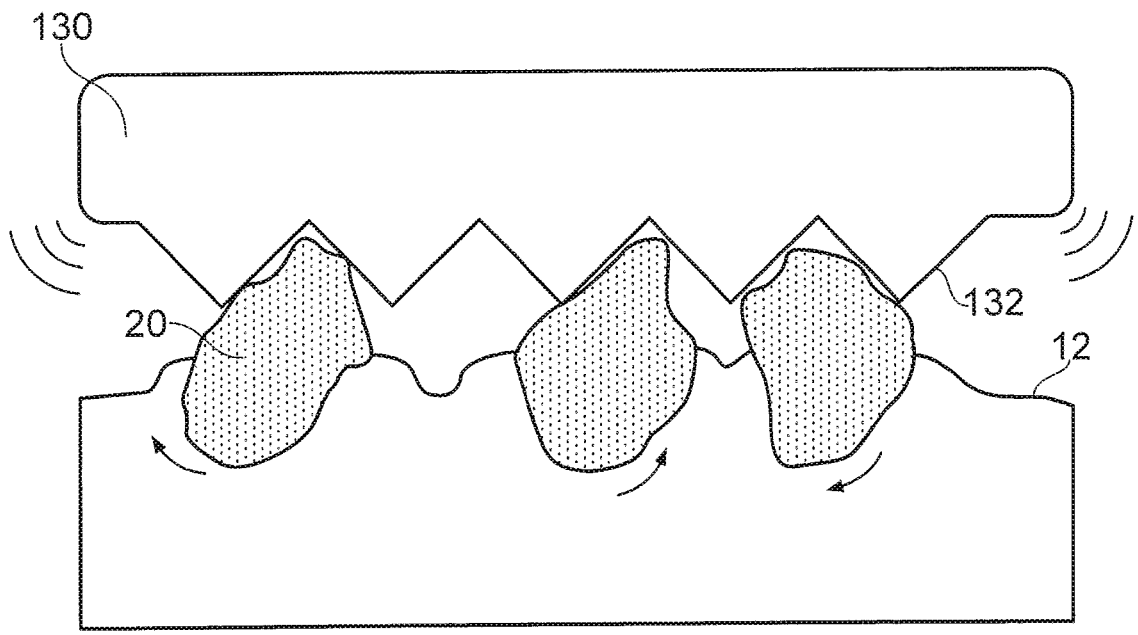
FIG. 6 shows a side view of the press and the particles being embedded into the surface of the prosthetic component.

With reference to FIGS. 5 and 6, the ultrasonic vibrations at the sonotrode interface 134 will tend to orientate and embed the particles 20 so as to conform to the shape and surface texture of the sonotrode surface 132. For example, as shown in FIG. 5, if the sonotrode interface surface 132 is substantially flat and the geometric shape of the particles 20 have an aspect ratio greater than 1, this can result in the particles laying flat along their length, instead of protruding vertically. This can lead to a reduction in the roughness of the coating, which may be undesirable since the success of osteofixation may depend on the roughness of the implant surface, particularly regarding the initial primary fixation of the component within the patient's bone.

Therefore, as shown in FIG. 6, the pressing surface 132 may be textured to improve the roughness of the coating. For example, the surface 132 may comprise peaks and troughs, which may encourage the particles 20 to adopt a more vertical position.

Additionally or alternatively, the prosthetic component surface 12 may be textured, e.g. comprising peaks and troughs. The pressing surface 132 and/or prosthetic component surface 12 may be textured by moulding the respective component in a textured mould or any other method, such as sand blasting or machining.

By providing different surface textures at the sonotrode interface 134, the roughness of the coating may be controlled. In a preferred arrangement, the surface texture of the sonotrode surface 132 and/or component surface 12 is selected to provide a relatively rough surface texture with a topography of indents and protrusions similar in size to that of the bone attachment particle size (for example with a maximum dimension in the range of 200-350 µm) resulting in an optimum surface for fixation and osteointegration. In particular, the height difference between peaks and troughs of the textured surface 132, 12 may be more than approximately half of the typical particle size so that the textured surface may perform its function. Also, the height difference between peaks and troughs of the textured surface 132, 12 may be less than the minimum particle size to avoid the sonotrode contacting the prosthetic component surface. Accordingly, the height difference between peaks and troughs of the textured surface 132 may be substantially between 100 μm and 200 μm.

Although the exciter has been described above as comprising an ultrasonic exciter, the exciter may instead emit other forms of energy, for example electro-magnetic energy in the form of microwaves, infra-red radiation or high intensity light. Such energy may be emitted at a frequency or intensity or in a direction that excites the particles but not the prosthetic component directly.

In a further example, the particles may be heated by virtue of conduction from a surrounding medium, such as a fluid. The surrounding medium may be isolated from the prosthetic component so that prosthetic component is not directly heated by the medium, but only by the particles. In another example, the exciter may be configured to induce electric currents within the particles by virtue of a magnetic field. Such electric currents may increase the thermal energy of the particles.

However, regardless of how the particles are excited, the apparatus and method may be substantially similar to that described above, e.g. with an energy emitter, press and particle dispenser with any of the features described above. For example, the above-described ultrasonic emitter may simply be replaced with an alternative energy emitter. In particular, the energy emitter may be provided at one end of the press and the energy emitter may be adjacent to the interface with the prosthetic component.

Alternatively, the energy emitter and press may not be coupled together, e.g. they may be separate components spaced apart. The press may apply a pressure urging the particles into the prosthetic component and the energy emitter may excite the particles.

In short, the exciter of the present disclosure may be configured to increase the energy of the plurality of bone attachment particles at the same time without directly heating the prosthetic component. The increased energy of the particles may then melt the surface of the prosthetic component only in the vicinity of the particles. This reduces the heating of the prosthetic component and the effect on the component's material properties. Furthermore, since the energy may be applied to the bulk powder, a repeatable and fast manufacturing process is also provided.

The prosthetic component depicted may be an acetabular cup, e.g. for an artificial hip. However, the coating apparatus and method of the present disclosure may also be applied to: a prosthetic component for a knee, such as a cementless monoblock polyethylene tibial knee component; a prosthetic component for a shoulder, such as a monoblock glenoid component for shoulders; or any other prosthetic part for a human or animal body that is to be fixed to a bone.

It will be appreciated by those skilled in the art that although the invention has been described by way of example with reference to one or more examples, it is not limited to the disclosed examples and that alternative examples could be constructed without departing from the scope of the invention as defined by the appended claims.

The invention claimed is:

1. A method of applying a bone attachment coating to an orthopaedic implant, the bone attachment coating being formed from a plurality of particles applied to a polymer bone facing surface of the orthopaedic implant, the method comprising:
    locally exciting the plurality of particles applied to the orthopaedic implant using an ultrasonic exciter without directly exciting the polymer bone facing surface of the orthopaedic implant so as to increase the vibrational energy of the particles without directly heating the orthopaedic implant;
    wherein the vibrational energy of the particles causes localised heating of the orthopaedic implant such that the particles may be embedded into a bone facing region of the orthopaedic implant.

2. The method of claim 1, wherein the method further comprises:
    applying pressure by virtue of a press arranged to force the particles into the bone facing region of the orthopaedic implant.

3. The method of claim 1, wherein the method further comprises:
    using electro-magnetic energy to excite the particles.

4. The method of claim 1, wherein the method further comprises:
    heating the particles.

5. The method of claim 4, wherein the method further comprises:
    using a magnetic field to induce electric currents within the particles.

6. The method of claim 1, wherein the method further comprises:
    providing the particles at an interface between the ultrasonic exciter and the orthopaedic implant.

7. The method of claim 6, wherein the method further comprises:
    dispensing the particles from a dispenser.

8. The method of claim 7, wherein the method further comprises:
    permitting the particles to flow from the dispenser to the interface by virtue of at least one of gravity and an applied pressure.

9. The method of claim 8, wherein the method further comprises:
    agitating at least one of the dispenser and particles so as to encourage the flow of the particles from the dispenser.

10. The method of claim 9, wherein the method further comprises:
    providing the particles at the interface between the ultrasonic exciter and the orthopaedic implant by virtue of carrying the particles in a flow of a fluid.

11. The method of claim 1, wherein the method further comprises:
    moving at least one of the orthopaedic implant and the ultrasonic exciter so that the particles are applied over the polymer bone facing surface of the orthopaedic implant.

12. The method of claim 11, wherein the method further comprises:
    rotating the orthopaedic implant and the ultrasonic exciter relative to one another.

13. The method of claim 12, wherein the method further comprises:
    rotating the orthopaedic implant and the ultrasonic exciter relative to one another about a. first axis of the orthopaedic implant.

14. The method of claim 13, wherein the method further comprises:
    rotating the orthopaedic implant and the ultrasonic exciter relative to one another about a second axis of the orthopaedic implant.

15. The method of claim 14, wherein the method further comprises:

adjusting a rotational rate about the first or second axis according to a position of the orthopaedic implant about the second or first axis respectively.

16. A method of applying a bone attachment coating to an orthopaedic implant, the bone attachment coating being formed from a plurality of particles applied to a polymer bone facing surface of the orthopaedic implant, the method comprising:
    locally exciting the plurality of particles using an ultrasonic exciter without directly exciting the polymer bone facing surface of the orthopaedic implant so as to increase the vibrational energy of the particles without directly heating the orthopaedic implant;
    wherein the vibrational energy is selected to be lower than an amount of energy required to melt the particles; and
    wherein the vibrational energy of the particles causes localised heating of the orthopaedic implant by an amount sufficient to melt the polymer bone facing surface such that the particles may become embedded into a bone facing region of the orthopaedic implant.

17. The method of claim 16, wherein the orthopaedic implant comprises a hip implant, a knee implant, or a shoulder implant.

18. The method of claim 16, further comprising, prior to applying the plurality of particles to the polymer bone facing surface, pre-treating the polymer bone facing surface to improve adhesion and to facilitate retention of the plurality of particles to the polymer bone facing surface.

19. The method of claim 16, further comprising contacting the particles with a textured pressing surface to apply a desired roughness to the bone attachment coating.

20. A method of applying a bone attachment coating to an orthopaedic implant, the bone attachment coating being formed from a plurality of particles applied to a polymer bone facing surface of the orthopaedic implant, the method comprising:
    locally exciting the plurality of particles using an ultrasonic exciter without directly exciting the polymer bone facing surface of the orthopaedic implant so as to increase the vibrational energy of the particles without directly heating the orthopaedic implant; and
    applying pressure to the particles using a press arranged so as to press the particles against the polymer bone facing surface of the orthopaedic implant at an interface between the press and the orthopaedic implant;
    wherein the vibrational energy of the particles causes localised heating of the orthopaedic implant and subsequent melting of the polymer bone facing surface such that the particles become embedded into a bone facing region of the orthopaedic implant.

* * * * *